United States Patent [19]
Eldridge

[11] Patent Number: 5,463,909
[45] Date of Patent: Nov. 7, 1995

[54] RUNOFF WATER SAMPLER

[75] Inventor: Jess S. Eldridge, Eden Prairie, Minn.

[73] Assignee: Minnesota Mining and Manufacturing Company, St. Paul, Minn.

[21] Appl. No.: 213,225

[22] Filed: Mar. 15, 1994

[51] Int. Cl.$^6$ .................................................. G01N 1/14
[52] U.S. Cl. ........................... 73/864.52; 73/864.34
[58] Field of Search ........................ 73/864.34, 864.35, 73/864.52, 864.53, 864.54, 864.63

[56] References Cited

U.S. PATENT DOCUMENTS

| | | | |
|---|---|---|---|
| 3,589,197 | 11/1969 | Brooks, Sr. | 73/864.35 |
| 4,195,524 | 4/1980 | Hansen | 73/864.52 |
| 4,958,528 | 9/1990 | Garrison . | |
| 5,197,340 | 3/1993 | Jones | 73/864.35 |

OTHER PUBLICATIONS

ISCO Automatic Sampler (Sales Bulletin).
Sigma Automatic Sampler (Sales Bulletin).
Edmund Buhler Automatic Sampler (Sales Bulletin).
EPIC Automatic Sampler (Sales Bulletin).
Brailsford Automatic Samplers (Sales Bulletin).
Global Water (Sales Bulletin).

*Primary Examiner*—Richard Chilcot
*Assistant Examiner*—Max H. Noori
*Attorney, Agent, or Firm*—Gary L. Griswold; Walter N. Kirn; Robert H. Brink

[57] ABSTRACT

A device for collecting liquid samples is disclosed. The device can be set up such that it does not collect any sample until it detects the presence of water at the sample site. The sample can then be drawn by suction into a previously evacuated container. The device is particularly well suited for collection of storm water runoff samples.

9 Claims, 3 Drawing Sheets

RUNOFF WATER SAMPLER

FIELD OF THE INVENTION

This invention relates to devices for collecting a quantity of runoff water. In another aspect it relates to methods for collecting a quantity of runoff water.

BACKGROUND OF THE INVENTION

The detrimental effects of pollution are well known. Pollution takes many forms including water pollution. In order to combat such pollution, it is desirable to know what levels of pollution exist in what areas.

In order to compile data on water pollution, the U.S. Environmental Protection Agency has proposed regulations which may require manufacturing plants to monitor the pollution they emit. Such monitoring may include the collection and analysis of storm water runoff. In some cases it is desirable to sample a quantity of the first runoff water. In other cases it is desirable to sample the water which has already been flowing for a certain amount of time rather than merely sampling the first occurrence of water. The use of a mere bucket is insufficient, as this would allow the sample, once collected, to be circulated out.

Devices for the collection of runoff water are commercially available. Such devices include those made by EDMUND BUHLER GmbH & Co., ISCO CO. (Lincoln, Nebr.), SIGMA, Sonford, Brailsford & Company, Inc. (Rye, N.Y.), and Global Water (Fair Oaks, Calif.).

U.S. Pat. No. 4,958,528 (Garrison) discloses a device for collecting runoff water comprising a means for automatically blocking the entry of water into the device when more than a predetermined quantity of water has entered the device. Such device is said to be inexpensive and to require no electric source.

BRIEF SUMMARY OF THE INVENTION

Briefly, in one aspect, this invention provides a liquid collection device which can collect and store a quantity of liquid. A cavity is defined within a container, said cavity and container being capable of storing said liquid. Said container also being able to withstand subatmospheric pressure within said cavity. Attached to said container and in fluid communication with said cavity is a gas conduit, for example a series of connected tubes, defining a passageway adapted to allow a means for reducing pressure, for example an aspirator or a vacuum pump, to reduce the pressure within said cavity. Attached to said gas conduit and adapted to block and unblock its passageway is a valve. Attached to said container and in fluid communication with said cavity is a fluid conduit, for example a series of connected tubes, defining a passageway adapted to allow liquid to enter into said cavity. Attached to said liquid conduit and adapted to block and unblock its passageway is a valve which is connected to and in communication with a control means for automatically opening and closing this valve. Connected to and in communication with said control means is a detection means for detecting the presence of water.

The gas conduit and the liquid conduit can be the same or different. In other word there can be two conduits and two valves or there can be one conduit and one valve. This is because in use, a single conduit could first be used to remove air from the cavity and second to draw liquid into the cavity. These two uses do not occur at the same time so one passageway can be used for both. Through much of this specification we will discuss the conduits as if there are two, but it should be kept in mind that there can be just one conduit and one valve.

The container is such that in operation it can be sealed so that the only access to the cavity is through the gas conduit and/or the liquid conduit. The device is such that when the valves (either one or two depending on whether there is one or two conduits) are closed, air and liquid cannot pass into or out of the cavity, and subatmospheric pressure within the cavity, if any, is maintained.

In Another aspect, this invention provides a method for collecting liquid samples comprising the steps of (A) sealing access to the cavity such that the only access to the cavity is through the gas conduit; (B) reducing the pressure in the cavity in the device of this invention with a means for reducing pressure attached to said gas conduit, (C) blocking the passageway in the gas conduit by closing its valve so that the reduced pressure in the cavity is maintained; (D) placing the device, which now has reduced pressure in said cavity, at the site to be sampled; and (E) placing one end of said liquid conduit and one end of said detection means at the site where sampling is desired.

The present device is inexpensive, easy to use, and operates in correlation to the presence of run-off water. In other words, when there is run-off water to be sampled, the device will operate. The device does not require any power until activated (i.e., when liquid is detected).

BRIEF SUMMARY OF THE DRAWINGS

These and other advantages will be discussed with reference to the accompanying drawings, in which.

DETAILED DESCRIPTION

Figure 1:
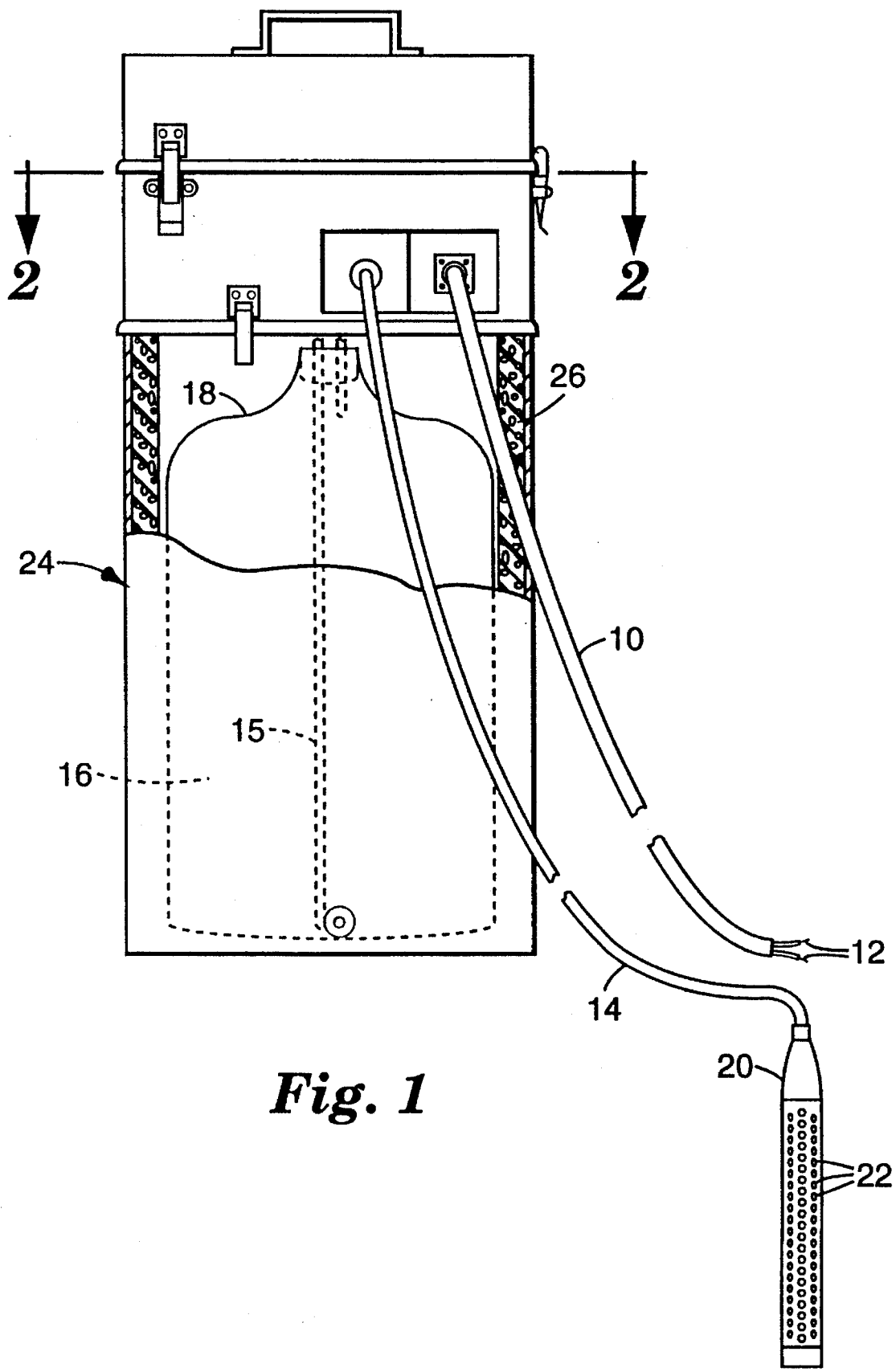
FIG. 1 shows a first embodiment of the invention in a side view partially broken away.
Figure 2:
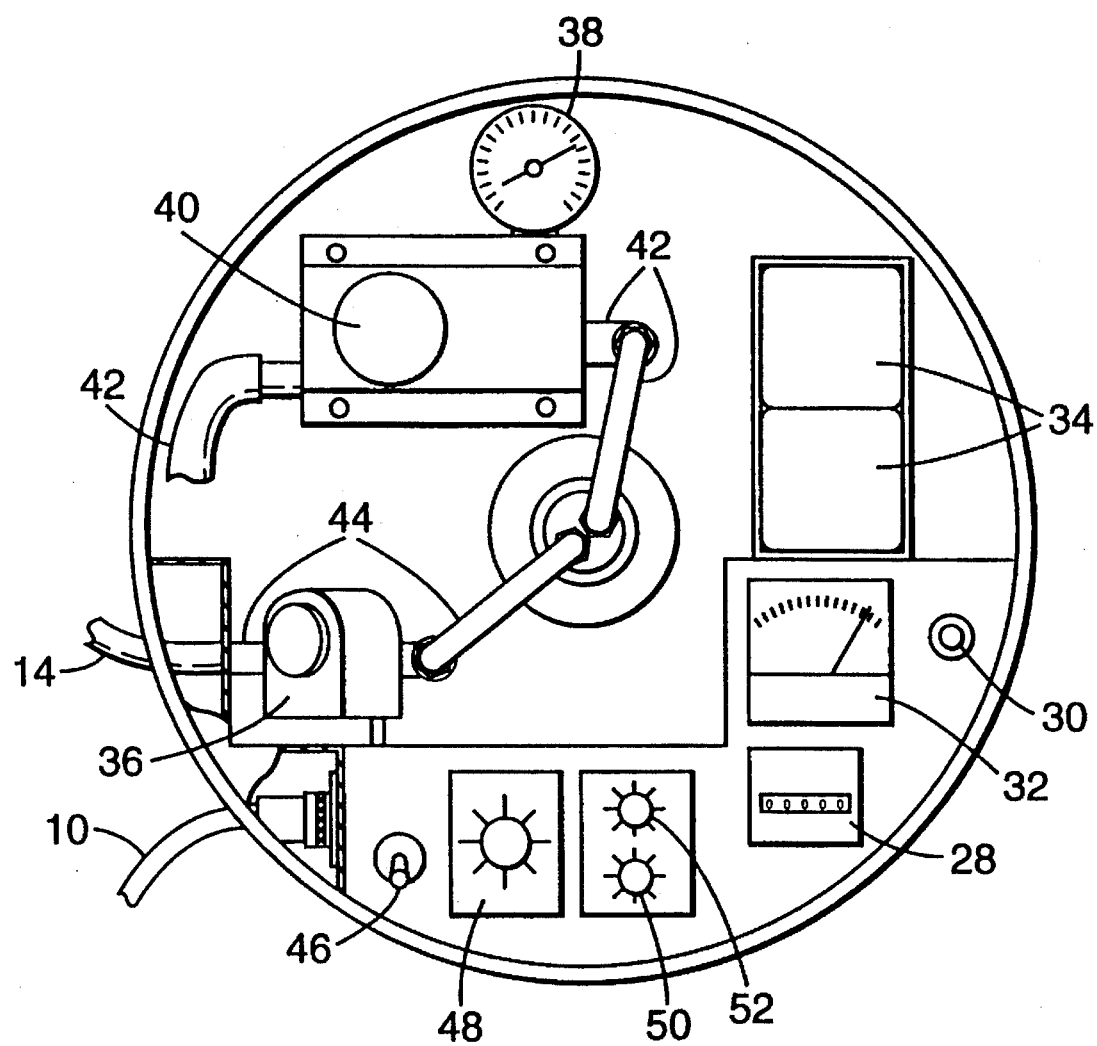
FIG. 2 shows a top view of this first embodiment taken along line 2—2 showing, among other things, optional devices for controlling the timing of sampling.
Figure 3:
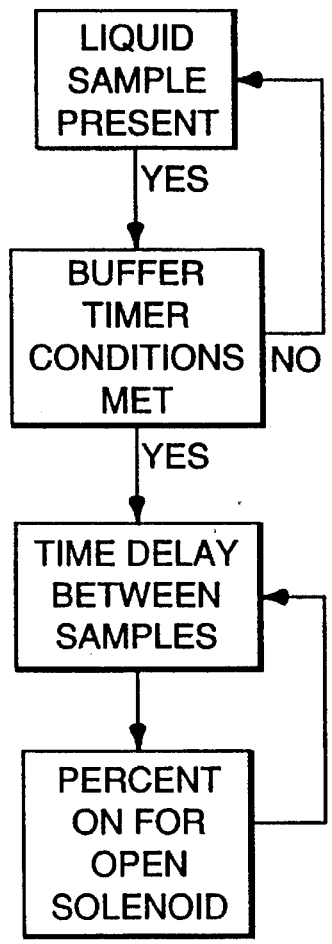
FIG. 3 is a flow diagram illustrating, in one embodiment, how sampling occurs when the optional devices for controlling the timing of sampling are used.
Figure 4:
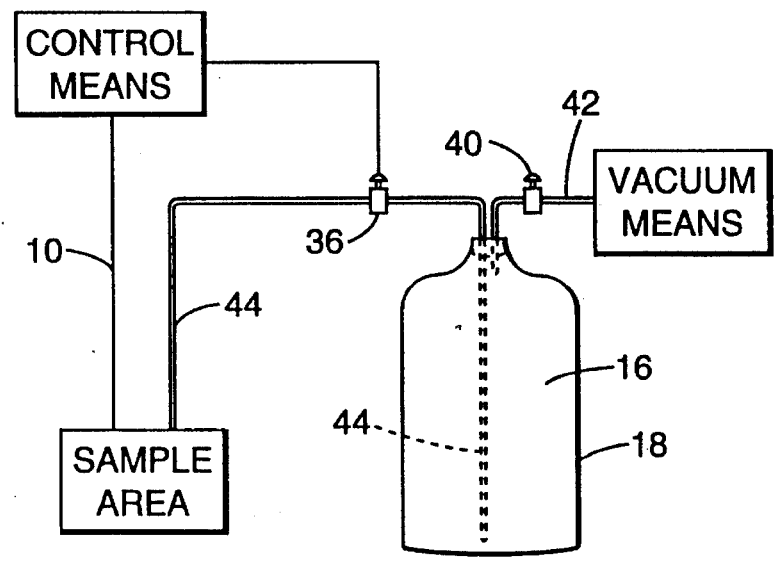
FIG. 4 is a schematic representation of one embodiment of the invention.

The container useful in this invention is capable of maintaining a subatmospheric pressure of at least 20 mm Hg without collapse or deformation of the cavity. Furthermore, said container should be constructed of materials that are impervious to and inert to any materials that will be analyzed for. Examples of generally suitable materials for the container are glass, stainless steel, and polyvinylchloride. The shape of the cavity is generally immaterial. The volume of the cavity should be appropriate for the amount of liquid sample that is desired to be collected, with the understanding the container will not become completely full of liquid because a perfect vacuum will not be achieved in the cavity. The container will define interior walls defining the cavity. The container will be such that the cavity can be sealed so that in use access to the cavity is only through said gas conduit and said liquid conduit and only when said valve or valves are open.

Said means to reduce the pressure in said cavity can be any such device such as a vacuum pump or aspirator. Preferably such device can produce a subatmospheric pressure of at least 20 mm Hg in said cavity. Although cavities of this invention maintained at subatmospheric pressures less than 20 mm Hg are useful, generally, the more the cavity is evacuated, the more preferred. This is because higher vacuum will generally allow for more samples to be taken and for samples to be taken at a higher velocity which is preferably because it reduces the precipitation of particles prior to the sample reaching the cavity.

Said conduits will generally be tubing. Such tubing can be a series of connected tubing, for example, Tygon tubing. The conduits must be capable of transporting gas and liquid without significant leakage of the gas or liquid. One end of the tube or series of tubes will be inside the cavity while the other end will be outside the cavity. The conduit or conduits define a passageway on the interior of the conduit through which gas and/or liquid can travel.

The end of the liquid conduit outside the cavity can be used to draw in liquid samples and can optionally further comprise an end piece to add weight to that end of the conduit to help anchor said end and prevent excessive movement. The end piece can also define holes in order to act as a filter to help prevent the conduit from becoming clogged. Preferably, such holes are smaller than the inside diameter of the passageway defined by the liquid conduit.

Said valve or valves can be any valve such as those conventionally used for such purposes, for example a solenoid valve, that will block the cavity from outside air and liquid when closed but will allow liquid and air to enter the cavity when open. The valve for the gas conduit can be one that is controlled manually or automatically. The valve for the liquid conduit must be capable of automatic control so that it can be controlled by the control means.

Said means for detecting water can be anything that will detect and communicate the presence of water for example, a float switch, or simple bare wires such that a circuit is completed when the wires are bridged by water. Such means can be placed at the sample site to indicate to the control means when water is present on the sample site.

Said control means for automatically opening and closing said second valve are generally timers such as those generally available. Said control means will need a power source such as a battery. Batteries are useful because they are portable and self contained. Said control means preferably comprises timing means that allow for extensive control of the liquid conduit valve. In other words, it is preferred to have timing means to open and shut the liquid conduit valve when certain pre-set conditions are met. Such means for extensive control are illustrated in FIG. 2.

The device of this invention can further comprise a housing which contains said container. Said housing can be insulated to protect collected samples from heat and cold that might affect the contents of the samples.

Presently preferred embodiments will be described in detail with reference to the accompanying drawings. FIG. 1 shows a preferred embodiment of the invention where the detection means 10 contains simple bare wires 12 where the wires 12 are connected to a power source, such as batteries, and the presence of water bridges the wires 12 and completes a circuit, thus indicating the presence of water. In the embodiment shown in FIG. 1, there are two conduits and two corresponding valves. The liquid conduit comprises several connected sections of tube, including tubes 14 and 15, that will allow the sample to flow up and into the container 18 and down to the bottom of the cavity 16. The end of tube 15 inside the cavity 16 goes to the bottom, or near the bottom, of the cavity 16 in order to reduce turbulence and splashing which could cause undesirable aeration of the sample as it enters the cavity 16. The end of tube 14 outside the cavity 16, the sampling end of the series of tubes, is provided with an end piece 20 that adds weight to the sampling end of tube 14 in order to reduce movement of the tube 14. The end piece 20 defines holes 22 smaller than the inside diameter of tube 14 in order to reduce the chances of a large object entering the tube 14 and clogging it. FIG. 1 also shows the container 18 inside a housing 24 which contains insulation 26.

FIG. 2 shows a top view of a preferred embodiment comprising devices for controlling the timing of sampling. The counter 28 counts the number of times the valve 36 for the liquid conduit 44 was opened. Batteries 34 can be used as the power source for the opening and closing of valve 36. The voltage test button 30 and volt meter 32 allow for testing of the batteries 34 to ensure that they are still operational. The vacuum gauge 38 shows how much vacuum is in the cavity 16. The gas conduit 42 can be connected to a vacuum pump, aspirator, or other means for reducing the pressure in the cavity 16. The valve 40 blocks the passageway in the gas conduit and closes off access to the cavity 16 after the cavity 16 has been evacuated. The gas conduit 42 and the liquid conduit 44 comprise several sections of connected tubing.

FIG. 2 shows several means that allow for extensive control of valve 36 and therefore of when and for how long samples are taken. The main on/off switch 46 can be used to turn the control system on or off. The buffer timer 48 can be set to require that water be continuously detected by the detection means 10 for a specified period of time or no sample is taken. For example, you may want to require that water be present for at least 1 minute or no samples will be taken. The off timer 50 can be set to specify the period of time that valve 36 stays closed before the first sample is taken and between successive sample. The % on timer 52 can be set to specify the period of time that valve 36 stays open to take in a sample. In operation the device would then open and close according the % on and off timers 50 and 52 until no vacuum remained. This control of valve 36 is illustrated in FIG. 3.

In the method of this invention, pressure in the cavity of the device of this invention is reduced by a means for reducing pressure attached to said gas conduit, and maintained by closing said valve or valves. The device, which then has reduced pressure in said cavity, is placed at the site to be sampled, and one end of said liquid conduit and said detection means are placed at the site where sampling is desired.

FIG. 4 is a schematic representation of one embodiment of the device of this invention. This particular embodiment has two conduits and two corresponding valves. FIG. 4 also illustrates one embodiment of the method of this invention. In the method of this invention, valve 36 is closed, valve 40 is open, the gas conduit 42 is connected to a vacuum means which reduces the pressure in the cavity 16. The valve 40 is then closed in order, along with the closed liquid valve 36, to maintain vacuum inside the cavity 16. The vacuum means can then be removed and the device is then placed near the sample site. One end of the liquid conduit 44 and the detecting means 10 are placed at the sample site in the area where sampling is desired or expected. Then, when water is present in the sample area long enough to meet the pre-set timing requirements, if any, then the control means causes valve 36 to open and a sample is drawn by vacuum pressure into the cavity 16.

If desired optional timing controls such as the buffer timer 48, % off timer 50, and the % on timer 52, illustrated in FIG.

2, can be set to desired time periods prior to placing the device at the sampling site.

If preferred, more than one device can be used at a single sampling site, for example, in order to sample with different timing controls. For example, two devices could be used with the first device set with a buffer timer time of 0.6 minutes, a % off timer time of 1 minute, and the % on timer could be set to stay open until the cavity is filled. The second device could be set at a buffer timer time of 0.6 minutes, a % off timer time of 20 minutes, and a % on timer time of 10 seconds.

Various modifications and alterations of this invention will become apparent to those skilled in the art without departing from the scope and spirit of this invention.

What is claimed is:

1. A liquid collection device, comprising: (A) a cavity defined within a container, said cavity being capable of storing liquid and being able to withstand subatmospheric pressure of at least 20 mm Hg within said cavity; (B) attached to said container and in fluid communication with said cavity, a gas conduit which defines a passageway suitable for the transportation of gases and adapted to allow a means for reducing pressure to reduce the pressure within said cavity; (C) a valve attached to said gas conduit and adapted to block and unblock said passageway defined by said gas conduit; (D) attached to said container and in fluid communication with said cavity, a liquid conduit which defines a passageway suitable for the transportation of liquid; (E) a valve attached to said liquid conduit and adapted to block and unblock said passageway defined by said liquid conduit, wherein said valve is adapted to be automatically controlled; (F) in communication with the valve that is attached to the liquid conduit, a control means to automatically open and shut the valve that is attached to the liquid conduit; and (G) outside of said cavity, a detection means for detecting the presence of water at a sampling site outside said device, connected to and in communication with said control means; wherein said device can be sealed such that the only access to the cavity by liquid or gas is through said passageways.

2. The device of claim 1 further comprising an insulated housing which surrounds said container.

3. The device of claim 1 wherein said control means comprises timing means.

4. The device of claim 1 wherein said container is glass.

5. The device of claim 1 wherein the gas conduit and the liquid conduit are two separate conduits.

6. The device of claim 1 wherein said conduits are a series of connected tubes.

7. The device of claim 1 wherein said device is capable of maintaining pressure of 20 mm Hg below atmospheric pressure within said cavity.

8. A method for collecting liquid samples using the device of claim 1, comprising the steps of (A) sealing said device such that the only access to the cavity is through the gas conduit; (B) reducing the pressure in the cavity in the device with a means for reducing pressure attached to said gas conduit; (C) blocking the passageway in the gas conduit by closing its valve so that the reduced pressure in the cavity is maintained; (D) placing the device, which now has reduced pressure in said cavity, at the site to be sampled; and (E) placing on end of said liquid conduit and said detection means at the site where sampling is desired.

9. The method of claim 8 wherein the pressure in the cavity reduced to, and is maintained at, at least 20 mm Hg less than atmospheric pressure until sample is detected.

\* \* \* \* \*